(12) United States Patent
Steidler

(10) Patent No.: US 7,601,799 B2
(45) Date of Patent: Oct. 13, 2009

(54) METHODS AND MEANS TO PROMOTE GUT ABSORPTION

(75) Inventor: Lothar Steidler, Bandon (IE)

(73) Assignee: Actogenix N.V., Zwijnaarde (BE)

( * ) Notice: Subject to any disclaimer, the term of this patent is extended or adjusted under 35 U.S.C. 154(b) by 192 days.

(21) Appl. No.: 11/018,188

(22) Filed: Dec. 20, 2004

(65) Prior Publication Data

US 2005/0158282 A1 Jul. 21, 2005

Related U.S. Application Data

(63) Continuation of application No. PCT/EP03/50424, filed on Jun. 19, 2003.

(30) Foreign Application Priority Data

Jun. 19, 2002 (EP) .................................. 02077532

(51) Int. Cl.
*A61K 38/00* (2006.01)
*C07K 14/00* (2006.01)
*C12N 5/10* (2006.01)
*C12N 15/00* (2006.01)

(52) U.S. Cl. ....................... 530/300; 530/350; 435/360; 435/320.1

(58) Field of Classification Search ................. 530/300, 530/350; 535/300; 424/243.1, 234.1; 435/360, 435/320.1; 935/22, 27, 55
See application file for complete search history.

(56) References Cited

U.S. PATENT DOCUMENTS

| | | | |
|---|---|---|---|
| 4,100,495 A | 7/1978 | Luvison et al. |
| 4,190,495 A | 2/1980 | Curtiss, III |
| 4,888,170 A | 12/1989 | Curtiss, III |
| 5,032,510 A | 7/1991 | Kovacevic et al. |
| 5,149,532 A | 9/1992 | Brunell |
| 5,240,705 A | 8/1993 | Jacobs |
| 5,288,703 A | 2/1994 | Wilmore |
| 5,330,753 A | 7/1994 | Mekalanos et al. |
| 5,364,774 A | 11/1994 | Muir et al. |
| 5,401,642 A | 3/1995 | Fiers et al. |
| 5,401,658 A | 3/1995 | Fiers et al. |
| 5,417,986 A | 5/1995 | Reid et al. |
| 5,455,034 A | 10/1995 | Nagaraja et al. |
| 5,504,005 A | 4/1996 | Bloom et al. |
| 5,547,664 A | 8/1996 | Charles et al. |
| 5,559,007 A | 9/1996 | Suri et al. |
| 5,591,632 A | 1/1997 | O'Donnell et al. |
| 5,733,540 A | 3/1998 | Lee |
| 5,753,622 A | 5/1998 | Buret et al. |
| 5,824,538 A | 10/1998 | Branstrom et al. |
| 5,972,685 A | 10/1999 | Beitz et al. |
| 5,972,887 A | 10/1999 | Schwartz |
| 6,130,082 A | 10/2000 | Majarian et al. |
| 6,190,662 B1 | 2/2001 | Steidler et al. |
| 6,190,669 B1 | 2/2001 | Noriega et al. |
| 6,221,648 B1 | 4/2001 | Le Page et al. |
| 6,261,561 B1 | 7/2001 | Stewart et al. |
| 6,605,286 B2 | 8/2003 | Steidler |
| 6,656,907 B1 | 12/2003 | Buret et al. |
| 6,746,671 B2 | 6/2004 | Steidler et al. |
| 2001/0006642 A1* | 7/2001 | Steidler et al. ........... 424/243.1 |
| 2004/0043003 A1 | 3/2004 | Chen et al. |

FOREIGN PATENT DOCUMENTS

| | | |
|---|---|---|
| DE | 42 31 764 A1 | 3/1994 |
| EP | 0 176 320 | 4/1986 |
| EP | 0 406 003 A1 | 1/1991 |
| EP | 0 449 770 | 10/1991 |
| EP | 0 450 176 | 10/1991 |
| EP | 1 092 437 A1 | 4/2001 |
| EP | 1 319 410 A1 | 6/2003 |
| GB | 2278358 A | 11/1994 |
| GB | WO 97/14806 * | 4/1997 |
| WO | WO 88/06626 | 9/1988 |
| WO | WO 90/00594 | 1/1990 |
| WO | WO 91/06654 | 5/1991 |
| WO | WO 93/17117 | 9/1993 |
| WO | WO 95/03418 | 2/1995 |
| WO | WO 95/10614 | 4/1995 |
| WO | WO 95/10621 | 4/1995 |
| WO | WO 96/11277 | 4/1996 |
| WO | WO 96/40947 | 12/1996 |
| WO | WO 97/14806 | 4/1997 |
| WO | WO 98/31786 | 7/1998 |

(Continued)

OTHER PUBLICATIONS

Sham et al (Epidermal Growth Factor Improves Nutritional Outcome in a Rat Model of Short Bowel Syndrome, Journal of Pediatric Surgery, 2002; 37(5): 765-769).*

Wells, et al (Lactic acid bacteria as vaccine delivery vehicles, Antonie van Leeuwenhock, 1996; 70:17-330).*

Elliott et al (Bacterial colonization and healing of gastric ulcers: the effects of epidermal growth factor, Am. J. Physiol. Gastrointest. Liver Physiol., 2000; 278:G105-G112).*

Eizaguirre et al (Effect of Growth Hormone, Epidermal Growth Factor, and Insulin on Bacterial Translocation in Experimental Short Bowel Syndrome, Journal of Pediatric Surgery, 2000; 35(5): 692-695).*

Wells et al (Lactic acid bacteria as vaccine delivery vehicles, Antonie van Leeuwenhock, 1996; 70: 317-330).*

(Continued)

*Primary Examiner*—Robert B Mondesi
*Assistant Examiner*—Lakia J Tongue
(74) *Attorney, Agent, or Firm*—TraskBritt

(57) ABSTRACT

The present invention relates to epidermal growth factor (EGF) producing lactic acid bacteria and their use to increase intestinal villi height and to promote gut absorption. In particular, the invention relates to EGF producing *Lactococcus lactis* and *Lactobacillus casei*. The organisms may be especially useful to treat Short Bowel Syndrome.

3 Claims, 3 Drawing Sheets

FOREIGN PATENT DOCUMENTS

| WO | WO 99/58652 | 11/1999 |
|---|---|---|
| WO | WO 00/01799 | 1/2000 |
| WO | WO 00/18377 | 4/2000 |
| WO | WO 00/22909 | 4/2000 |
| WO | WO 00/23471 | 4/2000 |
| WO | WO 02/0090551 A2 | 11/2002 |
| WO | WO 2004-001020 A2 | 12/2003 |
| WO | WO 2004/046346 | 6/2004 |

OTHER PUBLICATIONS

Sham et (Epidermal Growth Factor Improves Nutritional Outcome in a Rat Model of Short Bowel Syndrome, Journal of Pediatric Surgery, 2002; 37(5): 765-769).*
Hardin et al. (Gut, 1999; 44: 26-32).*
Stern et al. (Microscopy Research and Technique, 2000; 51: 138-148).*
Elliott et al., Bacterial colonization and healing of gastric ulcers: the effects of epidermal growth factor, Am J. Physiol. Gastrointest. Liver Physiol., 2000, pp. G105-G112, vol. 278.
PCT International Search Report, PCT/EP03/50242, dated Jan. 15, 2004.
Wells et al., Lactic acid bacteria as vaccine delivery vehicles, Antonie van Leeuwenhoek, 1996, pp. 317-330, vol. 70, No. 2-4, Kluwer Academic Publishers, the Netherlands.
Kurahayashi et al., Effects of EGF administration in the intestinal adaptation in the rat after massive intestinal resection, Diagnostics and New Medicaments, 1991, pp. 1691-1701, vol. 28, No. 9. Abstract only.
Bamba et al., Gastroenterol Jpn., 1993, pp. 511-517, vol. 28, No. 4.
Rao et al., Eur. J. Pharmacol., 1996, pp. 209-12, vol. 303, No. 3.
English translation of the Japanese Office Action dated Apr. 7, 2009.
U.S. Appl. No. 60/353,923, filed Jan. 31, 2002, Chen.
U.S. Appl. No. 60/353,964, filed Jan. 31, 2002, Chen.
U.S. Appl. No. 60/353,885, filed Jan. 31, 2002, Chen.
U.S. Appl. No. 60/401,465, filed Aug. 5, 2002, Chen.
Arslanoglu et al., 1998, Biotechnology Letters, pp. 917-921, vol. 20.
Boersma et al., (1995) "Lactobacillus as vectors with intrinsic adjuvanticity for safe live mucosal vaccines," Biochemistry Supplement 19A, p. 255.
Bojovic et al., Applied & Environ. Microbiol., 57/2:385-388(1991).
Brett et al., Eur. J. Immunol., 23:1608-1614 (1993).
Edwards et al., Infection & Immunity, 60/6:2514-2521 (1992).
Fu et al., Abstract "Development of a chromosome-plasmid balanced lethal system for Lactobacillus acidophilus with thyA gene as selective marker," Microbiol. Immunol., 2000, pp. 551-556, vol. 44, No. 7.
Gasson, Abstract, "In vivo genetic systems in lactic acid bacteria," FEMS Microbiol., 1990, Rev. 87:43-60.
Heath et al., Abstract. Cytokines as immunological adjuvants, Vaccine, 1992, pp. 427-34, vol. 10, No. 7.
Holmes et al., Infection & Immunity, 66/10:4633-4639 (1998).
Iwaki et al., Infection Immunity, 58/9:2929-2934 (1990).
Koivula et al., Isolation and Characterization of Lactococcus lactis subsp. lactis Promoters, Applied and Environmental Microbiology, Feb. 1991, pp. 333-340, vol. 57, No. 2.
Kong et al.. Secretion of Human Interleukin 2 by Recombinant Mycobacterium bovis BCG, Infection and Immunity, Mar. 1995. pp. 799-803. vol. 63, No. 3.
Leong et al., Selective Induction of Immune Responses by Cytokines Coexpressed in Recombinant Fowlpox Virus, Journal of Virology, Dec. 1994, pp. 8125-8130. vol. 68, No. 12.
Leong-Morgenthaler et al., Lactose Metabolism in Lactobacillus bulgaricus: Analysis of the Primary Structure and Expression of the Genes Involved, Journal of Bacteriology, Mar. 1991, pp. 1951-57. vol. 173. No. 6.
Norton et al., Fems Immunol. & Medical Nicrobiol. 14:167-177 (1996).
Norton et al., Fems Microbiol. Letters, 120:249-256 (1994).
Norton et al., Vaccine, 15/6-7:616-619 (1997).
Norton, (1995) "Progress in the Development of Lactococcus lactis as a Recombinant Mucosal Vaccine Delivery System," Folia Microbiol. 40:225-230.
PCT International Preliminary Examination Report, PCT/EP03/50832, dated Jul. 6, 2004.
PCT International Search Report, PCT/EP2005/052296, dated Sep. 5, 2005.
Rapoport, Current Opinion in Biotechnology, 1:21-27 (1990).
Robinson et al., Nature Biotechnology, 15:653-57 (1997).
Ross et al., Cloning and Characterization of the Thymidylate Synthase Gene from Lactococcus lactis subsp. lactis, Applied and Environmental Microbiology, Jul. 1990, pp. 2156-2163, vol. 56, No. 7.
Ross et al., Thymidylate Synthase Gene from Lactococcus lactis as a Genetic Marker: an Alternative to Antibiotic Resistance Genes, Applied and Environmental Microbiology, Jul. 1990, pp. 2164-2169, vol. 56. No. 7.
Salzet, Michel, "Leech Thrombin Inhibitors," Current Pharmacuetical Design, 2002, pp. 493-503, vol. 8.
Sasaki et al., "thyA as a Selection Marker in Construction of Food-Grade Host-Vector and Integration Systems for Streptococcus thermophilus," Applied and Environmental Microbiology, Mar. 2004, pp. 1858-1864, vol. 70, No. 3.
Schotte et al., Secretion of biologically active murine interleukin-10 by Lactococcus lactis, Enzyme and Microbial Technology, 2000, pp. 761-65. vol. 27.
Sibakov et al., Applied & Environ. Microbiol., 57/2:341-348 (1991).
Steidler et al., "Biological containment of genetically modified Lactococcus lactis for intestinal delivery of human interleukin 10," Nature Biotechnology, Jul. 2003, pp. 785-789, vol. 21, no. 7.
Steidler et al., "Treatment of Murine Colitis by Lactococcus lactis Secreting Interleukin-10," Science, Aug. 25, 2000, pp. 1352-1355, vol. 289.
Steidler et al., Secretion of Biologically Active Murine Interleukin-2by Lactococcus lactis subsp. lactis, Appl. Environ, Microbiol., 1995, 61:1627-1629.
Steidler et al., Infection & Immunity, 66/7:3183-3189 (1998).
Steidler et al., J. Bacteriol. 175/23:7639-7643 (1993).
Steidler et al., NATO ASI Series vol. H98, pp. 63-79 (1996).
Van De Guchte et al., Heterologous Gene Expression in Lactococcus lactis subsp. lactis: Synthesis, Secretion, and Processing of the Bacillus subtilis Neutral Protease, Applied and Environmental Microbiology, Sep. 1990, pp. 2606-2611, vol. 56, No. 9.
Wells et al., Applied & Environ. Microbiol., 59/11:3954-3959(1993).
Wells et al., Int. Dairy Journal, 5:1071-1079 (1995).
Wells et al., Molecular Microbiol. 8/6:1155-1162 (1993).
U.S. Patent Office Action for U.S. Appl. No. 10/687,996, notification date of Mar. 19, 2009.
U.S. Patent Office Action for U.S. Appl. No. 11/127,921, notification date of Mar. 10, 2009.
Bernudez-Humaran et al., J. Medical Microbiology, 2004, 53:427-433.
Bijlsma et al., Trends in Microbiology, 2003, 11/8:359-366.
Billman-Jacobe, Current Opinion in Biotechnology, 1996, 7:500-504.
Chen et al., FEMS Microbiology Letters, 2003, 229:111-117.
Claverys et al., Gene, 1995, 164:123-128.
Darji et al., J. Biotechnology, 1995, 43:205-212.
Farrell et al., FEMS Microbiology Letters, 1995, 130:81-85.
Figler et al., Archives Biochemistry and Biophysics, 2000, 376/1:34-46.
Fischetti et al.. Current Opinion in Biotechnology, Oct. 1993, 4/5:603-610.
Gotz, J. Applied Bacteriology Symposium Supplement, 1990. 49S-53S.
Gutierrez et al., Appl. Microbiol. Biotechnol., 2006, 72/1:41-51.
Hansson et al., J. Bacteriology, Jul. 1992, 174/13:4239-4245.
Hazebrouck et al., Applied and Environmental Microbiology, Dec. 2006, 72/12:7460-7467.
Hegedus et al., Gene, 1998, 207:241-249.
Janssen et al., Microbial Pathogenesis, 1995, 19:193-201.
Jeong et al., Food Microbiology, 2006, 23:82-89.

Leenhouts et al., Applied and Environmental Microbiology, Dec. 1998, 64/12:4736-4742.
Leenhouts et al., Applied and Environmental Microbiology, Sep. 1991, 57/9:2568-2575.
Leenhouts et al., I. Bacteriology, Aug. 1991, 173-15:4794-4798.
Liu et al., J. Applied Microbiology, 2005, 98:127-135.
Motamedi et al., Gene, 1995, 160:25-31.
Oggioni et al., Gene, 1996, 169:85-90.
Oggioni et al., Vaccine, 1995, 13/8:775-779.
Paccez et al., Vaccine, 2007, 24:4671-4680.
Platteeuw et al., Applied and Environmental Microbiology, 1996, 62/3:1008-1013.
Pouwels et al., International J. Food Microbiology, 1998, 41:155-167.
Pouwels et al., J. Biotechnology, 1996, 44:183-192.
Pozzi et al., Abstract, Research in Microbiology, 1990, 141/6:659-670.
Pozzi et al., Abstract, Research in Microbiology, 1992, 143/5:449-457.
Pozzi et al., Infection and Immunity, May 1992, 60/5:1902-1907.
Ramasany et al., Vaccine, 2006, 24:3900-08.
Reviriego et al., International Dairy Journal, 2007, 17-574-577.
Robinson et al., Nature Biology, Jul. 1997, 15:653-657.
Rodriguez et al., International J. Food Microbiology, 2003, 80:101-116.
Samuelson et al., J. Bacteriology, Mar. 1995, 177/6:1470-1476.
Slos et al., Fems Microbiology Letters, 1998, 169:29-36.
Thompson et al., Plasmid, 2001,46:188-201.
Van De Guchte et al., Applied and Environmental Microbiology, Jan. 1989, 55/1:224-228.
Van Mallaert et al., Med. Fac. Landbouww, Rijksuniv. Gent., 1989, 54(4b):1477-1485.
Waterfield et al., Gene, 1995, 165:9-15.
Williams et al., Plasmid, 2002, 47:241-245.
U.S. Appl. No. 10/687,996, filed Oct. 17, 2003, Lothar Steidler, Self-Contacting Lactobacillus Strain.
U.S. Appl. No. 11/127,921, filed May 12, 2005, Lothar Steidler, Self-Contacting Lactobacillus Strain.

* cited by examiner

SEQUENCE LISTING

```
<160> NUMBER OF SEQ ID NOS: 24

<210> SEQ ID NO 1
<211> LENGTH: 166
<212> TYPE: DNA
<213> ORGANISM: Homo sapiens
<220> FEATURE:
<221> NAME/KEY: CDS
<222> LOCATION: (1)..(150)
<223> OTHER INFORMATION:
<220> FEATURE:
<221> NAME/KEY: misc_feature
<223> OTHER INFORMATION: hEGF

<400> SEQUENCE: 1 aac tca gat tca gaa tgt cca ctt tca cac gat ggt tac tgt ttg cac        48
Asn Ser Asp Ser Glu Cys Pro Leu Ser His Asp Gly Tyr Cys Leu His
1               5                   10                  15 gat ggt gtt tgt atg tac atc gaa gct ctt gat aaa tac gct tgt aac        96
Asp Gly Val Cys Met Tyr Ile Glu Ala Leu Asp Lys Tyr Ala Cys Asn
            20                  25                  30 tgt gtt gtt ggt tac atc ggt gaa cgt tgt caa tac cgt gat ttg aaa       144
Cys Val Val Gly Tyr Ile Gly Glu Arg Cys Gln Tyr Arg Asp Leu Lys
        35                  40                  45 tgg tgg gaacttcgtt aactag                                              166
Trp Trp
    50

<210> SEQ ID NO 2
<211> LENGTH: 50
<212> TYPE: PRT
<213> ORGANISM: Homo sapiens
<220> FEATURE:
<221> NAME/KEY: misc_feature
<223> OTHER INFORMATION: hEGF

<400> SEQUENCE: 2

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp
    50

<210> SEQ ID NO 3
<211> LENGTH: 166
<212> TYPE: DNA
<213> ORGANISM: Mus musculus
<220> FEATURE:
```

```
<221> NAME/KEY: CDS
<222> LOCATION: (1)..(150)
<223> OTHER INFORMATION:
<220> FEATURE:
<221> NAME/KEY: misc_feature
<223> OTHER INFORMATION: mEGF

<400> SEQUENCE: 3
```

| aac | tca | tac | cca | ggt | tgt | cca | tca | tca | tac | gat | ggt | tac | tgt | ttg | aac | 48 |
|---|---|---|---|---|---|---|---|---|---|---|---|---|---|---|---|---|
| Asn | Ser | Tyr | Pro | Gly | Cys | Pro | Ser | Ser | Tyr | Asp | Gly | Tyr | Cys | Leu | Asn | |
| 1 | | | | 5 | | | | | 10 | | | | | 15 | | |

| ggt | ggt | gtt | tgt | atg | cac | atc | gaa | tca | ctt | gat | tca | tac | act | tgt | aac | 96 |
|---|---|---|---|---|---|---|---|---|---|---|---|---|---|---|---|---|
| Gly | Gly | Val | Cys | Met | His | Ile | Glu | Ser | Leu | Asp | Ser | Tyr | Thr | Cys | Asn | |
| | | | 20 | | | | | 25 | | | | | 30 | | | |

| tgt | gtt | atc | ggt | tac | tca | ggt | gat | cgt | tgt | caa | act | cgt | gat | ttg | cgt | 144 |
|---|---|---|---|---|---|---|---|---|---|---|---|---|---|---|---|---|
| Cys | Val | Ile | Gly | Tyr | Ser | Gly | Asp | Arg | Cys | Gln | Thr | Arg | Asp | Leu | Arg | |
| | | 35 | | | | | 40 | | | | | 45 | | | | |

| tgg | tgg | gaacttcgtt | aactag | | | | | | | | | | | | | 166 |
|---|---|---|---|---|---|---|---|---|---|---|---|---|---|---|---|---|
| Trp | Trp | | | | | | | | | | | | | | | |
| | 50 | | | | | | | | | | | | | | | |

```
<210> SEQ ID NO 4
<211> LENGTH: 50
<212> TYPE: PRT
<213> ORGANISM: Mus musculus
<220> FEATURE:
<221> NAME/KEY: misc_feature
<223> OTHER INFORMATION: mEGF

<400> SEQUENCE: 4
```

| Asn | Ser | Tyr | Pro | Gly | Cys | Pro | Ser | Ser | Tyr | Asp | Gly | Tyr | Cys | Leu | Asn |
|---|---|---|---|---|---|---|---|---|---|---|---|---|---|---|---|
| 1 | | | | 5 | | | | | 10 | | | | | 15 | |

| Gly | Gly | Val | Cys | Met | His | Ile | Glu | Ser | Leu | Asp | Ser | Tyr | Thr | Cys | Asn |
|---|---|---|---|---|---|---|---|---|---|---|---|---|---|---|---|
| | | | 20 | | | | | 25 | | | | | 30 | | |

| Cys | Val | Ile | Gly | Tyr | Ser | Gly | Asp | Arg | Cys | Gln | Thr | Arg | Asp | Leu | Arg |
|---|---|---|---|---|---|---|---|---|---|---|---|---|---|---|---|
| | | 35 | | | | | 40 | | | | | 45 | | | |

| Trp | Trp |
|---|---|
| | 50 |

```
<210> SEQ ID NO 5
<211> LENGTH: 40
<212> TYPE: DNA
<213> ORGANISM: Artificial Sequence
<220> FEATURE:
<223> OTHER INFORMATION: HEGF01

<400> SEQUENCE: 5
aactcagatt cagaatgtcc actttcacac gatggttact                            40

<210> SEQ ID NO 6
<211> LENGTH: 40
<212> TYPE: DNA
<213> ORGANISM: Artificial Sequence
<220> FEATURE:
<223> OTHER INFORMATION: HEGF02

<400> SEQUENCE: 6
gtttgcacga tggtgtttgt atgtacatcg aagctcttga                            40

<210> SEQ ID NO 7
<211> LENGTH: 40
<212> TYPE: DNA
<213> ORGANISM: Artificial Sequence
<220> FEATURE:
<223> OTHER INFORMATION: HEGF03
```

<400> SEQUENCE: 7
taaatacgct tgtaactgtg ttgttggtta catcggtgaa                                40

<210> SEQ ID NO 8
<211> LENGTH: 40
<212> TYPE: DNA
<213> ORGANISM: Artificial Sequence
<220> FEATURE:
<223> OTHER INFORMATION: HEGF04

<400> SEQUENCE: 8
cgttgtcaat accgtgattt gaatggtgg gaacttcgtt                                 40

<210> SEQ ID NO 9
<211> LENGTH: 20
<212> TYPE: DNA
<213> ORGANISM: Artificial Sequence
<220> FEATURE:
<223> OTHER INFORMATION: HEGF05

<400> SEQUENCE: 9
aactagtctg cagaatctag                                                     20

<210> SEQ ID NO 10
<211> LENGTH: 40
<212> TYPE: DNA
<213> ORGANISM: Artificial Sequence
<220> FEATURE:
<223> OTHER INFORMATION: HEGF06

<400> SEQUENCE: 10
ctagattctg cagactagtt aacgaagttc ccaccatttc                                40

<210> SEQ ID NO 11
<211> LENGTH: 40
<212> TYPE: DNA
<213> ORGANISM: Artificial Sequence
<220> FEATURE:
<223> OTHER INFORMATION: HEGF07

<400> SEQUENCE: 11
aaatcacggt attgacaacg ttcaccgatg taaccaacaa                                40

<210> SEQ ID NO 12
<211> LENGTH: 40
<212> TYPE: DNA
<213> ORGANISM: Artificial Sequence
<220> FEATURE:
<223> OTHER INFORMATION: HEGF08

<400> SEQUENCE: 12
cacagttaca agcgtattta tcaagagctt cgatgtacat                                40

<210> SEQ ID NO 13
<211> LENGTH: 40
<212> TYPE: DNA
<213> ORGANISM: Artificial Sequence
<220> FEATURE:
<223> OTHER INFORMATION: HEGF09

<400> SEQUENCE: 13
acaaacacca tcgtgcaaac agtaaccatc gtgtgaaagt                                40

<210> SEQ ID NO 14

```
<211> LENGTH: 20
<212> TYPE: DNA
<213> ORGANISM: Artificial Sequence
<220> FEATURE:
<223> OTHER INFORMATION: HEGF10

<400> SEQUENCE: 14
ggacattctg aatctgagtt                                                   20

<210> SEQ ID NO 15
<211> LENGTH: 40
<212> TYPE: DNA
<213> ORGANISM: Artificial Sequence
<220> FEATURE:
<223> OTHER INFORMATION: MEGF01

<400> SEQUENCE: 15
aactcatacc caggttgtcc atcatcatac gatggttact                             40

<210> SEQ ID NO 16
<211> LENGTH: 40
<212> TYPE: DNA
<213> ORGANISM: Artificial Sequence
<220> FEATURE:
<223> OTHER INFORMATION: MEGF02

<400> SEQUENCE: 16
gtttgaacgg tggtgtttgt atgcacatcg aatcacttga                             40

<210> SEQ ID NO 17
<211> LENGTH: 40
<212> TYPE: DNA
<213> ORGANISM: Artificial Sequence
<220> FEATURE:
<223> OTHER INFORMATION: MEGF03

<400> SEQUENCE: 17
ttcatacact tgtaactgtg ttatcggtta ctcaggtgat                             40

<210> SEQ ID NO 18
<211> LENGTH: 40
<212> TYPE: DNA
<213> ORGANISM: Artificial Sequence
<220> FEATURE:
<223> OTHER INFORMATION: MEGF04

<400> SEQUENCE: 18
cgttgtcaaa ctcgtgattt gcgttggtgg gaacttcgtt                             40

<210> SEQ ID NO 19
<211> LENGTH: 20
<212> TYPE: DNA
<213> ORGANISM: Artificial Sequence
<220> FEATURE:
<223> OTHER INFORMATION: MEGF05

<400> SEQUENCE: 19
aactagtctg cagaatctag                                                   20

<210> SEQ ID NO 20
<211> LENGTH: 40
<212> TYPE: DNA
<213> ORGANISM: Artificial Sequence
<220> FEATURE:
<223> OTHER INFORMATION: MEGF06

<400> SEQUENCE: 20
```

```
ctagattctg cagactagtt aacgaagttc ccaccaacgc                    40
```

<210> SEQ ID NO 21
<211> LENGTH: 40
<212> TYPE: DNA
<213> ORGANISM: Artificial Sequence
<220> FEATURE:
<223> OTHER INFORMATION: MEGF07

<400> SEQUENCE: 21

```
aaatcacgag tttgacaacg atcacctgag taaccgataa                    40
```

<210> SEQ ID NO 22
<211> LENGTH: 40
<212> TYPE: DNA
<213> ORGANISM: Artificial Sequence
<220> FEATURE:
<223> OTHER INFORMATION: MEGF08

<400> SEQUENCE: 22

```
cacagttaca agtgtatgaa tcaagtgatt cgatgtgcat                    40
```

<210> SEQ ID NO 23
<211> LENGTH: 40
<212> TYPE: DNA
<213> ORGANISM: Artificial Sequence
<220> FEATURE:
<223> OTHER INFORMATION: MEGF09

<400> SEQUENCE: 23

```
acaaacacca ccgttcaaac agtaaccatc gtatgatgat                    40
```

<210> SEQ ID NO 24
<211> LENGTH: 20
<212> TYPE: DNA
<213> ORGANISM: Artificial Sequence
<220> FEATURE:
<223> OTHER INFORMATION: MEGF10

<400> SEQUENCE: 24

```
ggacaacctg ggtatgagtt                                          20
```

METHODS AND MEANS TO PROMOTE GUT ABSORPTION

CROSS-REFERENCE TO RELATED APPLICATION

This application is a continuation of PCT International Patent Application No. PCT/EP2003/050424, filed on Jun. 19, 2003, designating the United States of America, and published, in English, as PCT International Publication No. WO 2004/01020 A2 on Dec. 31, 2003, the contents of the entirety of which is incorporated by this reference.

TECHNICAL FIELD

The present invention relates generally to biotechnology, and, more particularly, to epidermal growth factor (EGF) producing lactic acid bacteria and their use to increase intestinal villi height and to promote gut absorption. In particular, the invention relates to EGF producing *Lactococcus lactis* and *Lactobacillus casei*. These organisms may be especially useful to treat Short Bowel Syndrome.

BACKGROUND

The efficiency of gut absorption is essential for good food conversion. Gut adsorption is largely determined by the gut surface, which is a function, amongst others, of the length of the gut and the height of the villi. In cases where an operative removal of a part of the gut is necessary, as in the case of cancer or Crohn's disease, this may result in decreased gut adsorption, resulting in insufficient food conversion and a shortage of nutrients, dehydration and even potentially lethal metabolic changes. These syndromes caused by the extensive resection of the small intestine are known as "Short Bowel Syndrome."

Several methods have been proposed to improve the post-operational adaptation of, and to enhance, the gut absorption in patients with Short Bowel Syndrome. U.S. Pat. No. 5,288,703 discloses that both growth hormone and insulin-like growth factor have a positive effect on gut absorption in mammals. This positive effect can be enhanced by the administration of glutamine or a glutamine equivalent. Administration of glutamine and growth hormone results in an increase of the villi length (Gu et al., 2001; Zhou et al., 2001). U.S. Pat. No. 5,972,887 demonstrated a reversal of the reduced intestinal mucosal mass and absorptive function in patients by the administration of low doses of exogenous Hepatocyte Growth Factor. In addition, the glucagon-like peptides GLP-1 and GLP-2 have been used with positive results. Studies on laboratory animals (Scott et al., 1998), as well as on humans (Jeppesen et al., 2001), showed a positive correlation between an increase in concentration of GLP-2 and an improvement of the intestinal adaptation. Short Bowel patients, from whom the ileum has been removed, show a decrease in food-induced secretion of GLP-2 (Jeppesen et al., 1999). Those patients, especially, can be treated successfully with GLP-2. It has been shown that leptin also has a positive effect on intestinal adaptation in a rat model (Pearson et al., 2001).

A lot of interest has been paid to the effect of Epidermal Growth Factor (EGF, urogastron). EGF is a relatively acid stable hormone that is produced in the salivary and the Brunner's glands. It is found in a wide variety of external secretions, as well as in blood and amniotic fluid (Marti et al., 1989). The molecular weight of mature human EGF is 6.2 kDa (Carpenter et al., 1991). EGF is phylogenetically strongly conserved and is strongly cross-reactive between different species.

It is known that EGF increases the absorption of $H_2O$, $Na^+$, $Cl^-$ and glucose in a rabbit model (Opleta-Madsen et al., 1991). Moreover, EGF is stimulating the elongation of the villi. This results in an increase of the apical surface and a general increase in absorption of nutrients (Hardin et al., 1999). Absorption of carbohydrates is further facilitated by the EGF-stimulated secretion of pancreatic amylase (Piiper et al., 1994).

Several studies have shown a positive effect of the application of EGF in experimental animal models for Short Bowel Syndrome (Helmrath et al., 1988; Chaet et al., 1994; O'Loughlin et al, 1994; Swaniker et al., 1996; Lukish et al., 1997; Dunn et al., 1997).

EGF-mediated effects after intestinal resection are strongly dose dependent; up to a certain limit, the adaptation increases with increasing doses. In intestinal studies, the normal dose is situated between 30 and 300 µg/kg body weight/day. Systemic, as well as enteral, applications seem effective. However, systemic application may be unwanted for possible side effects; several neoplasmas do have EGF receptors and a general increase in EGF concentration in the blood might stimulate the formation of tumors. Enteral application of EGF, however, is less efficient as pepsin can process mature EGF into a truncated form that has only 25% of the initial biological activity (Playford et al., 1995).

DISCLOSURE OF THE INVENTION

Surprisingly, demonstrated is that EGF can be delivered in situ by recombinant lactic acid bacteria producing EGF. Efficient production and secretion of EGF by lactic acid bacteria is not evident, and needs optimization of the coding sequence. Moreover, it cannot be predicted that the lactic acid bacteria sufficiently survive the passage through the stomach to produce the appropriate amount of EGF to stimulate growth of the villi, to promote nutrient absorption and to treat the Short Bowel Syndrome.

It is a first aspect of the invention to provide an EGF producing lactic acid bacterium. Preferably, the lactic acid bacterium is secreting the EGF produced in the growth environment. Preferably, the lactic acid bacterium is a *Lactococcus lactis* or a *Lactobacillus casei*. Even more preferably, the lactic acid bacterium comprises SEQ ID NO:1 and/or SEQ ID NO:3 of the accompanying and incorporated herein SEQUENCE LISTING. A preferred embodiment is an EGF producing *Lactococcus lactis* comprising SEQ ID NO:3. Another preferred embodiment is an EGF producing *Lactobacillus casei* comprising SEQ ID NO:3.

Another aspect of the invention is the use of an EGF producing lactic acid bacterium according to the invention to promote gut absorption. Methods to measure gut absorption are known to the person skilled in the art. Still another aspect of the invention is the use of an EGF producing lactic acid bacterium according to the invention to treat the Short Bowel Syndrome. Preferably, the lactic acid bacterium according to the invention is applied orally; it may be treated by any treatment known to the person skilled in the art to improve its survival during the passage of the intestinal system. As a non-limiting example, it may be freeze-dried or spray dried and/or encapsulated in a suitable recipient so that the bacteria are only released in the small intestine. Encapsulation and treatments for delivery in the small intestine have been described, amongst others in U.S. Pat. No. 5,972,685, International Publication Nos. WO0018377 and WO0022909.

The lactic acid bacterium, according to the invention, may be combined with other compounds, having a positive effect on gut absorption and/or enhancing the positive effect of EGF. As a non-limited example, glutamine can be used in combination of the lactic acid bacterium according to the invention.

DETAILED DESCRIPTION OF THE INVENTION

EXAMPLES

Figure 1:
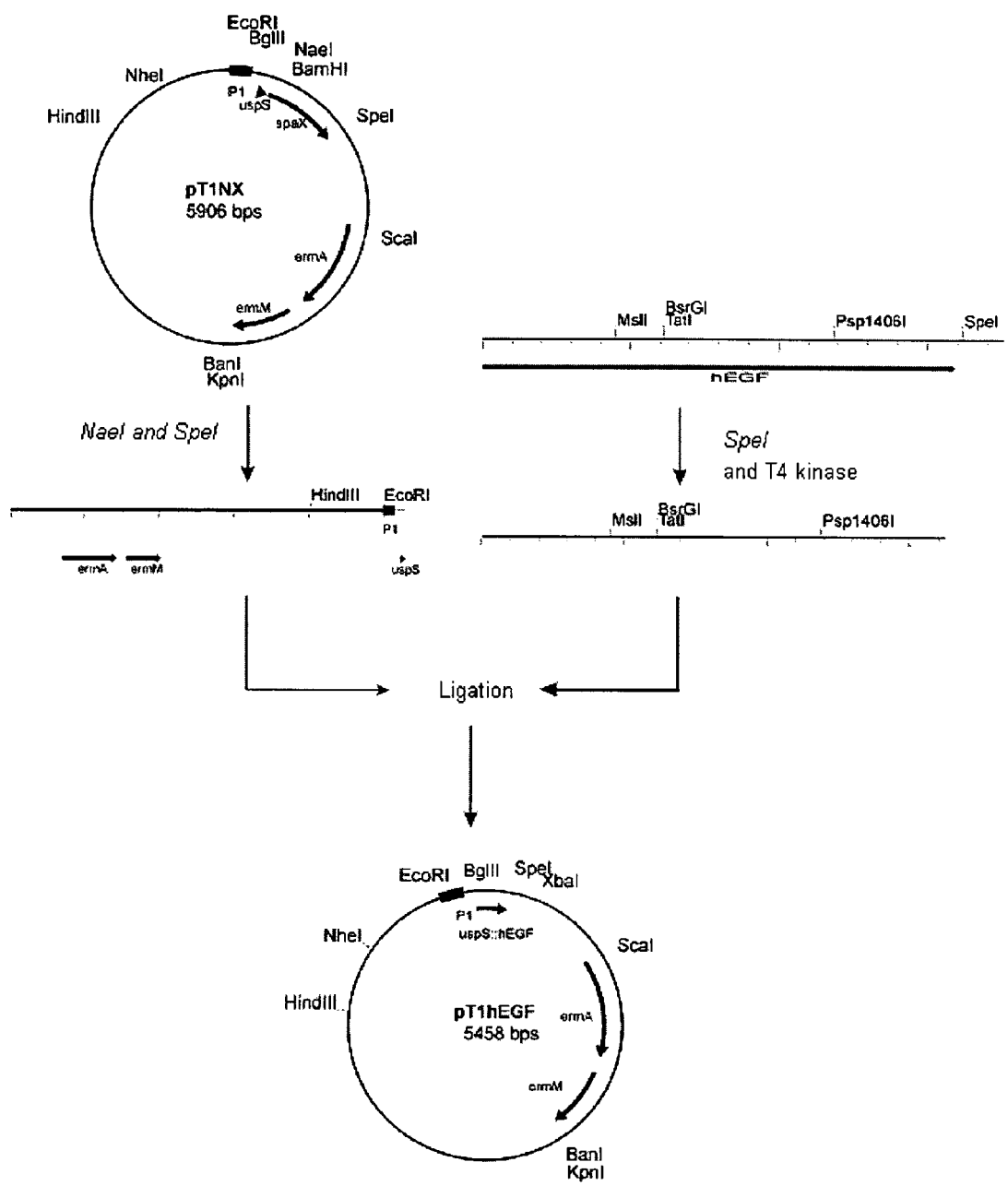
FIG. 1: Outline of the construction of pT1hEGF. The construction of pT1mEGF is carried out in a similar way.

Media and strains
M17:
5 g Bacto Tryptone
5 g Bacto Soytone
5 g Meat Digest
2.5 g Yeast Digest
0.5 g ascorbic acid
0.25 g $MgSO_4$
19 g disodium-β-glycerolphosphate
in 1 l deionized $H_2O$
GM17: M17 with 0.5% glucose
Recuperation medium:
1 ml 2×M1
0.5 ml 2 M sucrose
50 µl 20% glucose
40 µl 1 M $MgCl_2$
4 µl 1 M $CaCl_2$
406 µl $H_2O$
Agar medium is obtained by adding 1.2% agar
BM9 expression medium
60 g $Na_2HPO_4$
30 g $KH_2PO_4$,
10 g $NH_4Cl$
5 g NaCl.
50 Mm $CO_3$-buffer
2 mM $MgSO_4$
0.1 mM $CaCl_2$
0.5% casiton (Difco)
0.5% glucose
in 1 liter $H_2O$
*L. lactis* MG1363 is a plasmid and prophage free derivative of the *L. lactis* strain NCDO 712 (Gasson, 1983).

Example 1

Optimizing the EGF Coding Sequence for Expression in *Lactococcus*

Both the murine as well as the human EGF (accession number X04571 for hEGF and NM 010113 for mEGF) are available in the public databases at the National Center for Biotechnology Information (accession number X04571 for hEGF and NM_010113 for mEGF). The coding sequences were adapted to optimize the expression in *Lactococcus*. On the base of these sequences, primer sets were designed to assemble the optimized coding sequences of both hEGF and mEGF. At the 3' end of the coding sequence, a SpeI restriction site was introduced. The primers are shown in Table 1 (hEGF) and Table 2 (m EGF).

TABLE 1

| oligos used for assembly of hEGF, and the amount available |
|---|

Sense

| | | |
|---|---|---|
| HEGF01 | AACTCAGATTCAGAATGTCCACTTTCACACGATGGTTACT (SEQ ID NO:5) | 33.3 nmol |
| HEGF02 | GTTTGCACGATGGTGTTTGTATGTACATCGAAGCTCTTGA (SEQ ID NO:6) | 34.8 nmol |
| HEGF03 | TAAATACGCTTGTAACTGTGTTGTTGGTTACATCGGTGAA (SEQ ID NO:7) | 26.9 nmol |
| HEGF04 | CGTTGTCAATACCGTGATTTGAAATGGTGGGAACTTCGTT (SEQ ID NO:8) | 28.8 nmol |
| HEGF05 | AACTAGTCTGCAGAATCTAG (SEQ ID NO:9) | 29.7 nmol |

Antisense

| | | |
|---|---|---|
| HEGF06 | CTAGATTCTGCAGACTAGTTAACGAAGTTCCCACCATTTC (SEQ ID NO:10) | 31.1 nmol |
| HEGF07 | AAATCACGGTATTGACAACGTTCACCGATGTAACCAACAA (SEQ ID NO:11) | 22.5 nmol |
| HEGF08 | CACAGTTACAAGCGTATTTATCAAGAGCTTCGATGTACAT (SEQ ID NO:12) | 23.6 nmol |
| HEGF09 | ACAAACACCATCGTGCAAACAGTAACCATCGTGTGAAAGT (SEQ ID NO:13) | 28.4 nmol |

TABLE 1-continued oligos used for assembly of hEGF, and the amount available

| | | |
|---|---|---|
| HEGF10 | GGACATTCTGAATCTGAGTT<br>(SEQ ID NO:14) | 37.8 nmol |

TABLE 2 oligos used for assembly of mEGF, and the amount available

Sense

| | | |
|---|---|---|
| MEGF01 | AACTCATACCCAGGTTGTCCATCATCATACGATGGTTACT<br>(SEQ ID NO:15) | 29.7 nmol |
| MEGF02 | GTTTGAACGGTGGTGTTTGTATGCACATCGAATCACTTGA<br>(SEQ ID NO:16) | 28.0 nmol |
| MEGF03 | TTCATACACTTGTAACTGTGTTATCGGTTACTCAGGTGAT<br>(SEQ ID NO:17) | 20.0 nmol |
| MEGF04 | CGTTGTCAAACTCGTGATTTGCGTTGGTGGGAACTTCGTT<br>(SEQ ID NO:18) | 25.5 nmol |
| MEGF05 | AACTAGTCTGCAGAATCTAG<br>(SEQ ID NO:19) | 29.7 nmol |

Antisense

| | | |
|---|---|---|
| MEGF06 | CTAGATTCTGCAGACTAGTTAACGAAGTTCCCACCAACGC<br>(SEQ ID NO:20) | 33.4 nmol |
| MEGF07 | AAATCACGAGTTTGACAACGATCACCTGAGTAACCGATAA<br>(SEQ ID NO:21) | 30.2 nmol |
| MEGF08 | CACAGTTACAAGTGTATGAATCAAGTGATTCGATGTGCAT<br>(SEQ ID NO:22) | 27.3 nmol |
| MEGF09 | ACAAACACCACCGTTCAAACAGTAACCATCGTATGATGAT<br>(SEQ ID NO:23) | 26.2 nmol |
| MEGF10 | GGACAACCTGGGTATGAGTT<br>(SEQ ID NO:24) | 40.3 nmol |

The oligonucleotides were dissolved in water at a concentration of 100 µM, and used in a 10 times diluted concentration.

1 µl of each oligonucleotide is added to 10 µl Taq buffer, 8 µl 2 mM $Mg^{2+}$, 2 µl 0.5 mM XTP, 5 u Taq DNA polymerase (Boehringer, Mannheim, Germany) and 1 u Pfu DNA polymerase (Promega, Madison, USA). The reaction mixture is added up to 100 µl with water. The PCR reaction is carried out for 300 seconds at 94° C., followed by 30 times the cycle of 45 seconds at 94° C., 30 seconds at 48° C. and 30 seconds at 72° C., with a final step of 10 seconds at 15° C. After the assembly, hEGF and mEGF are amplified in a PCR mixture containing 1 µl Vent DNA-polymerase (New England Biolabs, Beverly, USA), 10 µl Taq buffer, 4 µl 0.5 mM XTP, 5 µl 0.5 µM of each primer, 1µl template DNA, 1 µl mM $Mg_2SO_4$ and 74 µl $H_2O$.

In the case of hEGF, HEGF01 and HEGF06 were used as primer; for mEGF, MEGF01 and MEGF06 were used. For hEGF, the same temperature schedule was used as for the first step. In the case of mEGF, the hybridization step was carried out at 52° C. in stead of 48° C.

After the assembly, the size of the optimized gene fragments was confirmed on a 2% agarose gel.

Example 2

Construction of pT1hEGF and pT1mEGF and transformation into *Lactococcus lactis*

SpeI cut assembled EGF (both for hEGF and mEGF) is ligated into a NaeI and SpeI digested pT1NX (Steidler et al., 1995), resulting in pT1hEGF and pT1mEGF. A schematic overview of the construction of pT1hEGF is shown in FIG. 1. Plasmids are transformed into competent cells of *L. lactis* by electroporation. 50 µl of cells are electroporated in a pre-cooled cuvet of 2 mm, at 25 µF, 2.5 kV and 400 Ω (Bio-Rad electroporator). *L. lactis* is made competent by growing a 1/100 dilution of a saturated culture, in 200 ml GM17 with 2.5% glycine, until an $OD_{600}$ of 0.5 (Wells et al., 1993). After electroporation, 1 ml of recuperation medium is added, and the cells are incubated for 1.5 hour at 28° C. Cells are plated on GM17 solid medium, comprising 5 µg/ml erythromycin.

For the transformation of *L. casei*, plasmid is isolated from *L. lactis* on a Qiagen-tip 100, according to the instructions of the manufacturer. The DNA is transformed into competent *L. casei* cells. *L. casei* cells are made competent by growing a 1/50 dilution of an overnight culture in 50 ml MRS (Oxoid LTD., Basingstoke, Hampshire, England) with 1% glycine at 37° C., untill an $OD_{600}$ of 0.6. The cells are harvested and washed twice with 10 ml 5 mM Na$_3$PO$_4$ pH 7.4, 1 mM MgCl$_2$, and resuspended in 500 μl electroporation buffer (0.3 M sucrose, 5 mM Na$_3$PO$_4$ pH 7.4, 1 mM MgCl$_2$). 10 μl of DNA is added to 50 μl of competent cells and the electroporation is carried out in a BioRad electroporator. After electroporation, 450 μl MRS is added and the cells are incubated for two hours at 37° C. Cells are plated on MRS agar with 5 μg/ml erythromycin. The presence of the plasmid is confirmed using PCR.

Example 3

Expression of EGF in *L. lactis* and *L. casei*

The transformed *L. lactis* strains MG1363 [pT1NX], MG1363 [pT1mEGF] and MG1363 [pT1hEGF] are pitched in 5 ml GM17 comprising 5 μg/ml erythromycin, and grown overnight at 30° C. This preculture is diluted 1/100 in 5 ml GM17 with erythromycin, and incubated for three hours at 28° C. The culture is centrifuged and resuspended in BM9 expression medium, and incubated overnight at 28° C. The transformed *L. casei* strains are grown under similar conditions, but using MRS as preculture, and BM9 as expression medium.

Figure 2A:
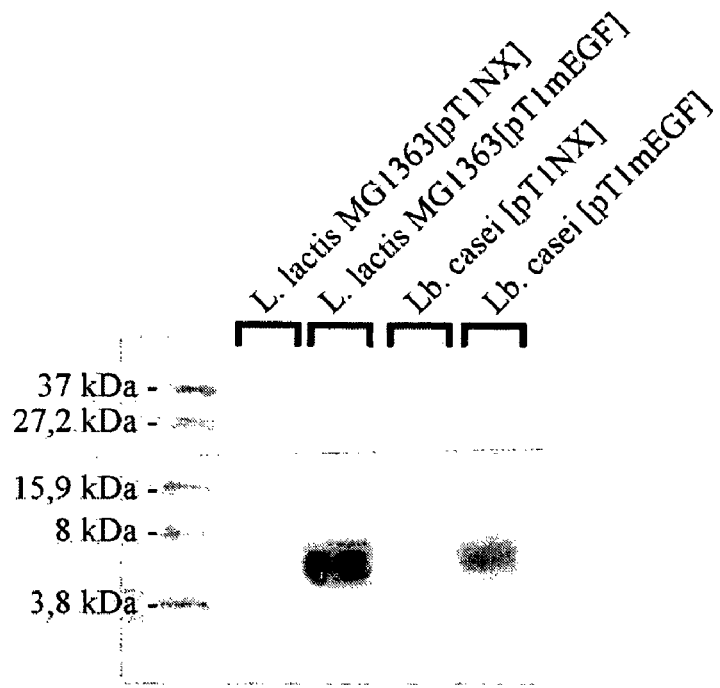
FIG. 2: Expression of mEGF (A) and hEGF (B) in *L. lactis* and *L. casei*. Supernatant of the cultures as indicated is separated on a 20% polyacrylamide gel and the proteins are detected using a Western blot.
Figure 2B:
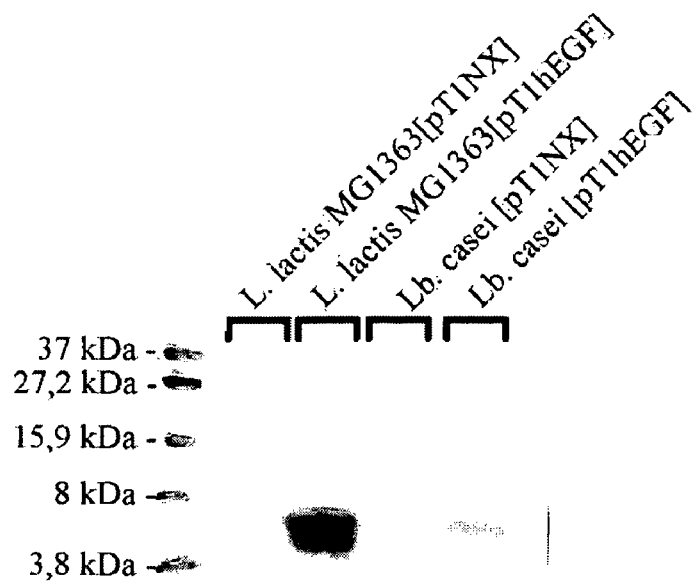

To the culture supernatant, ¹/₁₀ volume sodium desoxycholate is added, and the mixture is kept on ice for 10 minutes. ¹/₁₀ of volume 100% TCA is added and the mixture is incubated on ice for 15 minutes. After centrifugation, the pellet is dissolved in 50 μl H$_2$O and 50 μl 1 M Tris-HCl pH 9.5. The proteins are analyzed on a 20% Laemmli protein gel. Detection is carried out using a Western blot, with mouse polyclonal anti hEGF and rabbit anti mEGF as primary antibodies. Alkaline phosphatase labeled anti-mouse and anti-rabbit secondary antibodies were from Southern Biotechnology (Birmingham, USA). The results are summarized in FIG. 2.

Example 4

In Vivo Testing of Mice, Using the Transformed Lactic Acid Bacteria Strains

In order to assess the effect of the transformed lactic acid bacteria and the growth of the villi and the gut adsorption, seven groups of Balb/c mice (IFFA CREDO CR Broekman/Sulzfield) were treated either with a mEGF or hEGF expressing lactic acid bacterium strain. *L. lactis* and *L. casei* transformed with an empty vector pT1NX, or with BM9 medium was given to mice as a negative control.

600 μl of *L. casei* is pitched in 15 ml MRS with 10 μg/ml erythromycin. In the case of *L. lactis*, GM17 is used instead of MRS, and only 5 μg/ml erythromycin is used for selection. *L. casei* is incubated overnight at 37° C., for *L. lactis*, 30° C. is used. The overnight culture is harvested by centrifugation, and the pellet is resuspended in 1.5 ml BM9 expression medium. 100 μl of this solution is supplied daily, for a period of four weeks. At the end of the experiment, the mice are sacrificed and the intestine is isolated. The tissue is fixated in buffered formaldehyde and thin sections are colored using hematoxylin and eosin G, for microscopic analysis of the villi. The length of the villi is measured at several points to obtain a representative average. All sections were taken from the terminal ileum.

Figure 3:
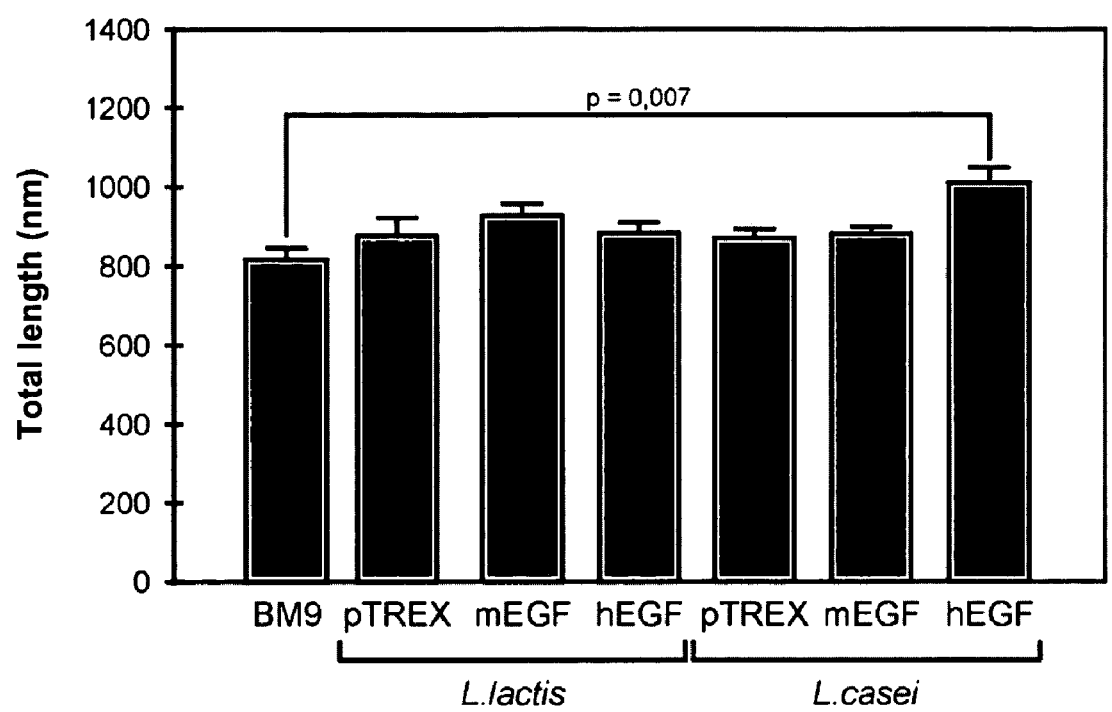
FIG. 3: Average villus length of the mice treated with either *Lactococcus lactis* or *Lactobacillus casei*, transformed with the empty vector pT1NX (pT1NX), with the vector pT1mEGF, expressing murine EGF (mEGF) or with the vector pT1hEGF expressing human EGF (hEGF). Medium BM9 treated mice are used as additional negative control (BM9).

The results are summarized in FIG. 3. *L. casei* [pT1hEGF], especially, has a positive effect on villus growth and should promote gut absorption.

REFERENCES

Carpenter C. D., Ingraham H. A., Cochet C., Walton G. M., Lazar C. S., Sodawski J. M., Rosenfeld M. G. and Gill G. N. (1991) Structural analysis of the transmembrane domain of the epidermal growth factor receptor. *J. Biol. Chem.* 266, 5750-5755.

Chaet M. S., Arya G., Ziegler M. M. and Warner B. W. (1994) Epidermal growth factor enhances intestinal adaptation after massive small bowel resection. *J. Pediatr. Surg.* 29, 1035-1039.

Chaet M. S., Arya G., Ziegler M. M. and Warner B. W. (1994) Epidermal growth factor enhances intestinal adaptation after massive small bowel resection. *J. Pediatr. Surg.* 29, 1035-1039.

Dunn J. C., Parungo C. P., Fonkalsrund E. W., McFadden D. W. and Ashley S. W. (1997) Epidermal growth factor selectively enhances functional enterocyte adaptation after massive small bowel resection. *J. Surg. Res.* 67, 90-93.

Gasson M. J. (1983) Plasmid complements of *Streptococcus lactis* NCDO 712 and other *lactic streptococci* after protoplast-induced curing. J. Bacteriol. 154, 1-9.

Gu Y., Wu Z. H., Xie J. X., Jin D. Y. and Zhuo H. C. (2001) Effects of growth hormone (rhGH) and glutamine supplemented parenteral nutrition on intestinal adaptation in short bowel rats. *Clin. Nutr.* 20, 159-166.

Hardin J. A., Chung B., O'Loughlin E. V. and Gal, D. G. (1999) The effect of epidermal growth factor on brush border surface area and function in the distal remnant following resection in the rabbit. *Gut* 44, 26-32.

Helmrath M. A., Shin C. E., Fox J. W., Erwin C. R. and Warner B. W. (1988) Adaptation after small bowel resection is attenuated by sialoadenectomy: the role for endogenous epidermal growth factor. *Surgery* 124, 848-854.

Jeppesen P. B., Hartmann B., Hansen B. S., Thulesen J., Holst J. J., Mortensen P. B. (1999) Impaired meal stimulated glucagon-like peptide 2 response in ileal resected short bowel patients with intestinal failure. *Gut* 45, 559-563.

Jeppesen P. B., Hartmann B., Thulesen J., Graff J., Lohmann J., Hansen B. S., Tofteng F., Poulsen S. S., Madsen J. L., Holst J. J. and Mortensen P. B. (2001) Glucagon-like peptide 2 improves nutrient absorption and nutritional status in short-bowel patients with no colon. *Gastroenterology* 120, 806-815.

Lukish J., Schwartz M. Z., Rushin J. M. and Riordan G. P. (1997) A comparison of the effect of growth factors on intestinal function and structure in short bowel syndrome. *J. Pediatr. Surg.* 32, 1652-1655.

Marti U., Burwen S. J. and Jones A. L. (1989) Biological effects of epidermal growth factor, with emphasis on the gastrointestinal tract and liver: an update. *Hepatology* 9, 126-138.

O'Loughlin E., Winter M., Shun A., Hardin J. A. and Gall D. G. (1994) Structural and functional adaptation following jejunal resection in rabbits: effect of epidermal growth factor. *Gastroenterology* 107, 87-93.

Opleta-Madsen K., Hardin J. and Gall D. G. (1991) Epidermal growth factor upregulates intestinal electrolyte and nutrient transport. *Am. J. Physiol.* 260, G807-814.

Pearson P. Y., O'Connor D. M. and Schwartz M. Z. (2001) Novel effect of leptin on small intestine adaptation. *J. Surg. Res.* 97, 192-195.

Piiper A., Stryjek-Kaminska D., Stein J., Caspary W. F. and Zeuzem S. (1994) Tyrphostins inhibit secretagogue-induced 1,4,5-IP3 production and amylase release in pancreatic acini. *Am. J. Physiol.* 266 G363-371.

Playford R. J., Marchbank T., Calnan D. P., Calam J., Royston P., Batten J. J. and Hansen H. F. (1995) Epidermal growth factor is digested to smaller, less active forms in acidic gastric juice. *Gastroenterology* 108, 92-101.

Scott R. B., Kirk D., MacNaughton W. K. and Meddings J. B. (1998) GLP-2 augments the adaptive response to massive intestinal resection in rat. *Am. J Physiol.* 275, G911-921.

Swaniker F., Guo W., Diamond J. and Fonkalsrud E. W. (1996) Delayed effects of epidermal growth factor after extensive small bowel resection. *J. Pediatr. Surg.* 31, 56-60.

Wells J. M., Wilson P. W. and Le Page R. W. (1993) Improved cloning vectors and transformation procedure for *Lactococcus lactis*. *J. Appl. Bacteriol.* 74, 629-636.

Zhou X., Li Y. X., Li N. and Li J. S. (2001) Effect of bowel rehabilitative therapy on structural adaptation of remnant small intestine: animal experiment. *World J. Gastroenterol.* 7, 66-73.

What is claimed is:

1. A method of enhancing villus growth in a subject, said method comprising:
   administering, to the subject, Epidermal Growth Factor (EGF)-producing *Lactobacillus casei* so as to enhance villus growth, wherein said EGF comprises SEQ ID NO:1.

2. A method of enhancing villus growth in a subject suffering from Short Bowel Syndrome, the method comprising:
   administering, to the subject, Epidermal Growth Factor (EGF)-producing *Lactobacillus casei* so as to enhance villus growth in the subject, wherein said EGF comprises SEQ ID NO:1.

3. A method of enhancing villus growth, the method comprising:
   applying orally Epidermal Growth Factor (EGF)-producing lactic acid bacteria to enhance villus growth, wherein the EGF-producing lactic acid bacteria comprise SEQ ID NO:1 wherein the EGF-producing lactic acid bacteria applied orally is *Lactobacillus casei*.

* * * * *

UNITED STATES PATENT AND TRADEMARK OFFICE
CERTIFICATE OF CORRECTION

PATENT NO. : 7,601,799 B2 Page 1 of 1
APPLICATION NO. : 11/018188
DATED : October 13, 2009
INVENTOR(S) : Lothar Steidler It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 204 days.

Signed and Sealed this

Fifth Day of October, 2010

David J. Kappos
*Director of the United States Patent and Trademark Office*